(12) United States Patent
Nomura et al.

(10) Patent No.: US 7,517,951 B2
(45) Date of Patent: Apr. 14, 2009

(54) MARKER PROTEINS FOR DIAGNOSING LIVER DISEASE AND METHOD OF DIAGNOSING LIVER DISEASE USING THE SAME

(75) Inventors: Fumio Nomura, Chiba (JP); Kazuyuki Sogawa, Chiba (JP); Takeshi Tomonaga, Chiba (JP); Takenori Ochiai, Chiba (JP); Hideaki Shimada, Chiba (JP); Tatsuya Ohashi, Chiba (JP); Katsuhiro Katayama, Chiba (JP)

(73) Assignee: Nitto Boseki Co., Ltd., Fukushima-Shi (JP)

( * ) Notice: Subject to any disclaimer, the term of this patent is extended or adjusted under 35 U.S.C. 154(b) by 407 days.

(21) Appl. No.: 10/538,916

(22) PCT Filed: Dec. 24, 2003

(86) PCT No.: PCT/JP03/16600

§ 371 (c)(1),
(2), (4) Date: Jun. 13, 2005

(87) PCT Pub. No.: WO2004/058966

PCT Pub. Date: Jul. 15, 2004

(65) Prior Publication Data

US 2006/0116504 A1   Jun. 1, 2006

(30) Foreign Application Priority Data

Dec. 24, 2002   (JP) .............................. 2002-371959

(51) Int. Cl.
*A61K 38/00*   (2006.01)
*A61K 35/14*   (2006.01)
(52) U.S. Cl. ...................................... 530/324; 530/382
(58) Field of Classification Search ....................... None
See application file for complete search history.

(56) References Cited

U.S. PATENT DOCUMENTS 5,639,940 A * 6/1997 Garner et al. .................. 800/7

FOREIGN PATENT DOCUMENTS

EP   1582873   10/2005
JP   63-237795   10/1988
WO   WO 94/16085 A2   7/1994
WO   WO 01/86304 A2   11/2001

OTHER PUBLICATIONS

Wells, Biochemistry, vol. 29, pp. 8509-8517, 1990.*
Seffernick et al., J. Bacteriology, vol. 138, pp. 2405-2410, 2001.*
F. Nomura, et al.; "Protein Chip Technology ni yoru Aratana Inshu Marker no Tansaku;" *Alcohol to Igaku Seibutsugaku*; vol. 23; Sep. 20, 2003; pp. 11-14.
T. Poynard, et al.; "A Simple Biological Index for Detection of Alcoholic Liver Disease in Drinkers;" *Gastroenterology*; vol. 100; No. 5 (Pt. 1); 1991; pp. 1397-1402.
F. Nomura, et al.; "Protein Chip Technology ni yoru Aratana Inshu Marker no Tansaku;" *Alcohol to Igaku Seibutsugaku*; vol. 23; Sep. 20, 2003; pp. 11-14.(see search report).
T. Poynard, et al.; "A Simple Biological Index for Detection of Alcoholic Liver Disease in Drinkers;" *Gastroenterology*; vol. 100; No. 5 (Pt. 1); 1991; pp. 1397-1402. (see search report).
Bedossa et al; "Apolipoprotein AI is a Serum and Tissue Marker of Liver Fibrosis in Alcoholic Patients," XP009068725; Alcoholism: Clinical and Experimental Research; vol. 13, No. 6 (Nov./Dec. 1989); pp. 829-833.
Pilette et al; "Histopathological evaluation of liver fibrosis: quantitative image analysis vs semi-quantitative scores, Comparison with Serum markers," XP002388410; J. Hepatology, 28 (1998) pp. 439-446.
European Search Report dated Jul. 21, 2006.

* cited by examiner

*Primary Examiner*—Suzanne M. Noakes
(74) *Attorney, Agent, or Firm*—Kratz, Quintos & Hanson, LLP

(57) ABSTRACT

Using the protein chip technology, biological samples such as sera are subjected to proteome analysis. Thus, a protein which is a human fibrinogen α-E chain decomposition product and has a molecular weight of 5,900, a protein which is an apolipoprotein AII decomposition product and has a molecular weight of 7,800, and a protein which is an apolipoprotein AI decomposition product and has a molecular weight of 28,000, each showing an increase or a decrease with the habit of drinking, are newly found out. By detecting or quantifying these proteins, a liver disease in a subject such as one having a problem of drinking can be diagnosed at the early stage.

1 Claim, 8 Drawing Sheets

1 MARKER PROTEIN
2 SERUN SAMPLE 1
3 SERUN SAMPLE 1
4 SERUN SAMPLE 2
5 SERUN SAMPLE 2
6 LOW-MOLECULAR WEIGHT MARKER
7 HIGH-MOLECULAR WEIGHT MARKER

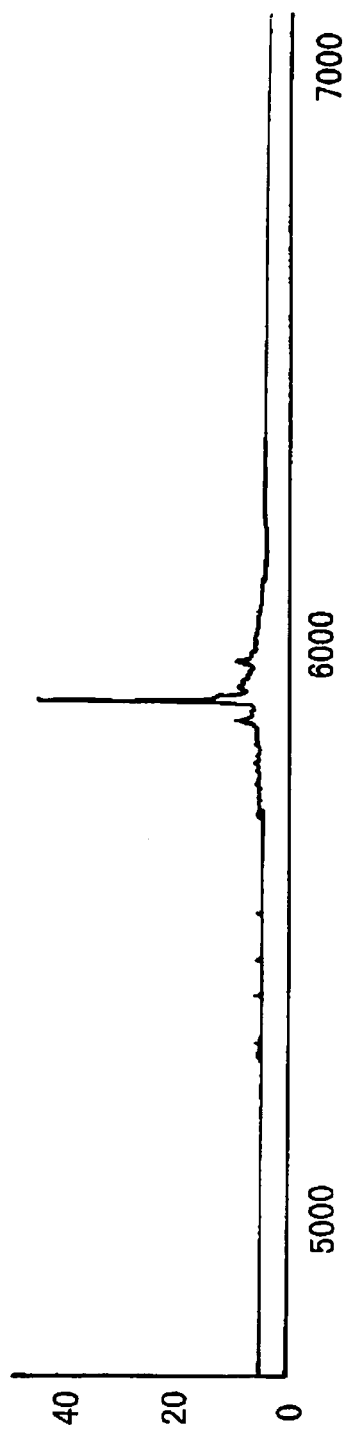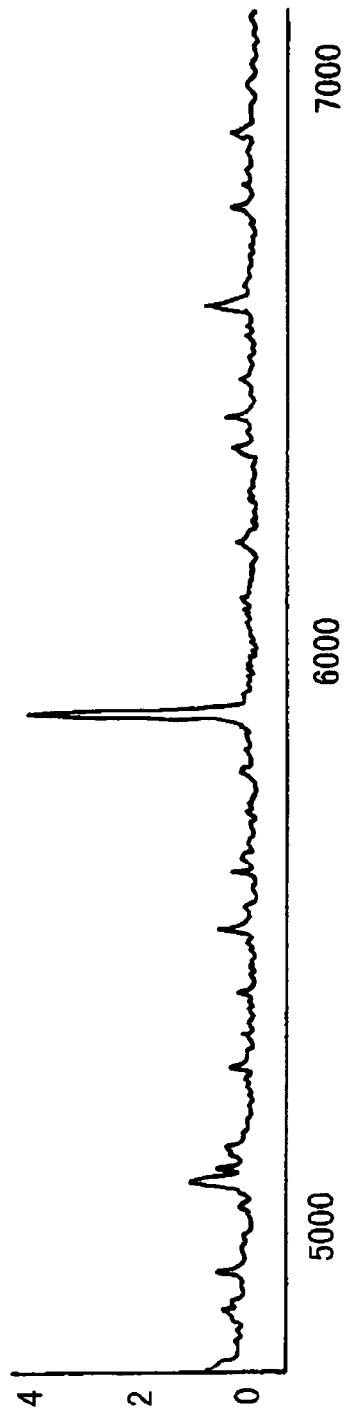
FIG.6

STANDARD CURVE FOR MEASUREMENT OF 5.9 kDa PROTEIN EIA METHOD

SEQUENCE LISTING

<160> NUMBER OF SEQ ID NOS: 3

<210> SEQ ID NO 1
<211> LENGTH: 54
<212> TYPE: PRT
<213> ORGANISM: Homo sapiens

<400> SEQUENCE: 1

Ser Ser Ser Tyr Ser Lys Gln Phe Thr Ser Ser Thr Ser Tyr Asn Arg
 1               5                  10                  15

Gly Asp Ser Thr Phe Glu Ser Lys Ser Tyr Lys Met Ala Asp Glu Ala
             20                  25                  30

Gly Ser Glu Ala Asp His Glu Gly Thr His Ser Thr Lys Arg Gly His
         35                  40                  45

Ala Lys Ser Arg Pro Val
     50

<210> SEQ ID NO 2
<211> LENGTH: 68
<212> TYPE: PRT
<213> ORGANISM: Homo sapiens

<400> SEQUENCE: 2

Glu Pro Cys Val Glu Ser Leu Val Ser Gln Tyr Phe Gln Thr Val Thr
 1               5                  10                  15

Asp Tyr Gly Lys Asp Leu Met Glu Lys Val Lys Ser Pro Glu Leu Gln
             20                  25                  30

Ala Glu Ala Lys Ser Tyr Phe Glu Lys Ser Lys Glu Gln Leu Thr Pro
         35                  40                  45

Leu Ile Lys Lys Ala Gly Thr Glu Leu Val Asn Phe Leu Ser Tyr Phe
     50                  55                  60

```
Val Glu Leu Gly
 65

<210> SEQ ID NO 3
<211> LENGTH: 243
<212> TYPE: PRT
<213> ORGANISM: Homo sapiens

<400> SEQUENCE: 3

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
     50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
                180                 185                 190

His Ala Lys Ala Thr Glu His Leu Ser Thr Leu Ser Glu Lys Ala Lys
            195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

MARKER PROTEINS FOR DIAGNOSING LIVER DISEASE AND METHOD OF DIAGNOSING LIVER DISEASE USING THE SAME

This application claims priority under 35 U.S.C. §119 of Japanese application No. 2002-371959, filed on Dec. 24, 2002.

TECHNICAL FIELD

The present invention relates to a plurality of serum proteins which have been found to increase or decrease with the habit of drinking and to be hence utilizable as marker proteins for diagnosing liver disease, as a result of proteome analysis of serum samples using the protein chip technology; and a method for diagnosing the probability of the onset of a liver disease, the liver disease, the prognosis of the liver disease, or the like in, for example, a problem drinker, by detecting or quantifying the above-mentioned proteins.

BACKGROUND ART

The first step to the diagnosis of an organ trouble caused by alcohol is to know an accurate drinking history, but alcohol dependence is called a denying disease, namely, an inveterate drinker does not accurately report his (or her) alcohol intake in all ages and countries. Therefore, an objective marker for substantiating the alcohol intake is necessary. A marker for the habit of drinking most commonly measured is γ-GTP (GGT). However, even if a drinker has a high GGT level, the GGT level does not always correlate with the degree of seriousness of liver trouble or the cumulative alcohol intake of the drinker. In addition, the change of GGT level after alcohol drinking is dependent on individuals and there are a considerable number of so-called nonresponders who show no GGT increase even after drinking a large amount of alcohol.

On the other hand, by a cause other than drinking, GGT is often increased also in a person having no drinking habit, such as a person having fatty liver due to fatness or a person who habitually takes a certain medicine. Guidance is often given, for example, in a hospital for complete physical examination so that a person having a high GGT level may be hastily judged to be a drinker. Therefore, chain-deficient transferrin (CDT) has been developed by investigators in north Europe for examination complementary to the examination with GGT, and its usefulness is emphasized in European and American references. But, in the case of the result obtained for Japanese, CDT as a marker of drinking permits detection of only about 10% of the GGT nonresponders.

Acetaldehyde, the first metabolite of ethanol is so reactive that it forms various acetaldehyde adducts of various proteins. For example, attempts have been made to detect an acetaldehyde-hemoglobin adduct by HPLC or the like. There is also an adduct that is expected to be an interesting marker capable of permitting estimation of alcohol intake in the past, such as HbAlc in the case of diabetes. But, such an adduct has not been put to practical use because of its low sensitivity.

The habit of drinking is one of two major causes of chronic liver troubles. As to liver cirrhosis cases in Japan, the percentage of cases due to only alcohol itself is considered to be only 10 to 15%. This, however, is data obtained mainly in university hospitals and the like. Considering the presence of alcoholics in a number estimated at more than 2,000,000, it is speculated that there are many latent patients with alcoholic liver trouble who have no chance to get a medical examination in a medical institution. In addition, since the habit of drinking is a factor of the exacerbation of cerebral hemorrhage, hypertension, gout and the like, early and accurate screening of problem drinkers is very important. However, as described above, there is no marker having decisive sensitivity and specificity among existing so-called markers of drinking, and hence searching for a novel marker is desired.

A general method for comprehensive expression protein analysis is two-dimensional protein electrophoresis, but this method is disadvantageous in the detection of low-molecular weight proteins or peptides. In recent years, a protein chip technology comprising a combination of surface enhanced laser desorption ionization (SELDI) and a time-of-flight mass spectrometer has been developed by Ciphergen Biosystems Inc., USA and has been begun to be clinically used for, for example, detecting a novel tumor marker. Therefore, comprehensive search for a novel marker by the utilization of such a proteomics technique and the like is desired.

DISCLOSURE OF THE INVENTION

The present invention is intended to find a novel marker capable of permitting early and accurate screening of the liver diseases of problem drinkers or the like, establish a system for measuring the marker and take advantage of the marker in medical treatment.

The present inventors have done intensive research on the above problem and consequently have accomplished the present invention. That is, the present inventors have succeeded in identifying novel serum proteins each of which shows an increase or a decrease with the habit of drinking, by the use of serum samples periodically collected from alcoholics hospitalized for giving up drinking. The present inventors have found that these serum proteins are utilizable as marker proteins for diagnosing liver disease, whereby the present invention has been accomplished.

Accordingly, the present invention relates to a marker protein for diagnosing liver disease selected from a protein which is a human fibrinogen α-E chain decomposition product and has a molecular weight of 5,900 (5.9 kDa protein), a protein which is an apolipoprotein AII decomposition product and has a molecular weight of 7,800 (7.8 kDa protein), a protein which is apolipoprotein AI and has a molecular weight of 28,000 and variants of these proteins which have the same function as that of the proteins as a marker protein for diagnosing liver disease.

In addition, the present invention relates to a method for diagnosing the probability of the onset of a liver disease, the liver disease or the prognosis of the liver disease by detecting or quantifying any of the above-mentioned marker proteins for diagnosing liver disease in a sample obtained from a patient who is suspected to have the liver disease.

Further, the present invention relates to a novel protein having the amino acid sequence shown as SEQ ID NO: 1 in the sequence listing, or its variant having the same function as that of said protein as a marker protein for diagnosing liver disease, which variant is a protein having 90% or more homology with said amino acid sequence or a protein having an amino acid sequence formed by deletion, substitution or addition of one or more amino acid residues in the amino acid sequence shown as SEQ ID NO: 1.

Still further, the present invention relates to a novel protein having the amino acid sequence shown as SEQ ID NO: 2 in the sequence listing, or its variant having the same function as that of said protein as a marker protein for diagnosing liver disease, which variant is a protein having 90% or more homology with said amino acid sequence or a protein having an amino acid sequence formed by deletion, substitution or addition of one or more amino acid residues in the amino acid sequence shown as SEQ ID NO: 2.

Still further, the present invention relates to a method for measuring any of the above-mentioned proteins or their variants by immunoassay by the use of an antibody against the protein or variant to be measured.

BRIEF DESCRIPTION OF DRAWINGS

FIG. 6 shows the result of comparing data for the synthetic 5.9 kDa protein with data for the serum of a patient who does not drink, by the use of WCXII protein chip arrays by utilizing Protein Chip System available from Ciphergen Biosystems Inc. Both of them show a peak at 5.9 kDa and they show the same behavior.

MODE FOR CARRYING OUT THE INVENTION

Figure 1:
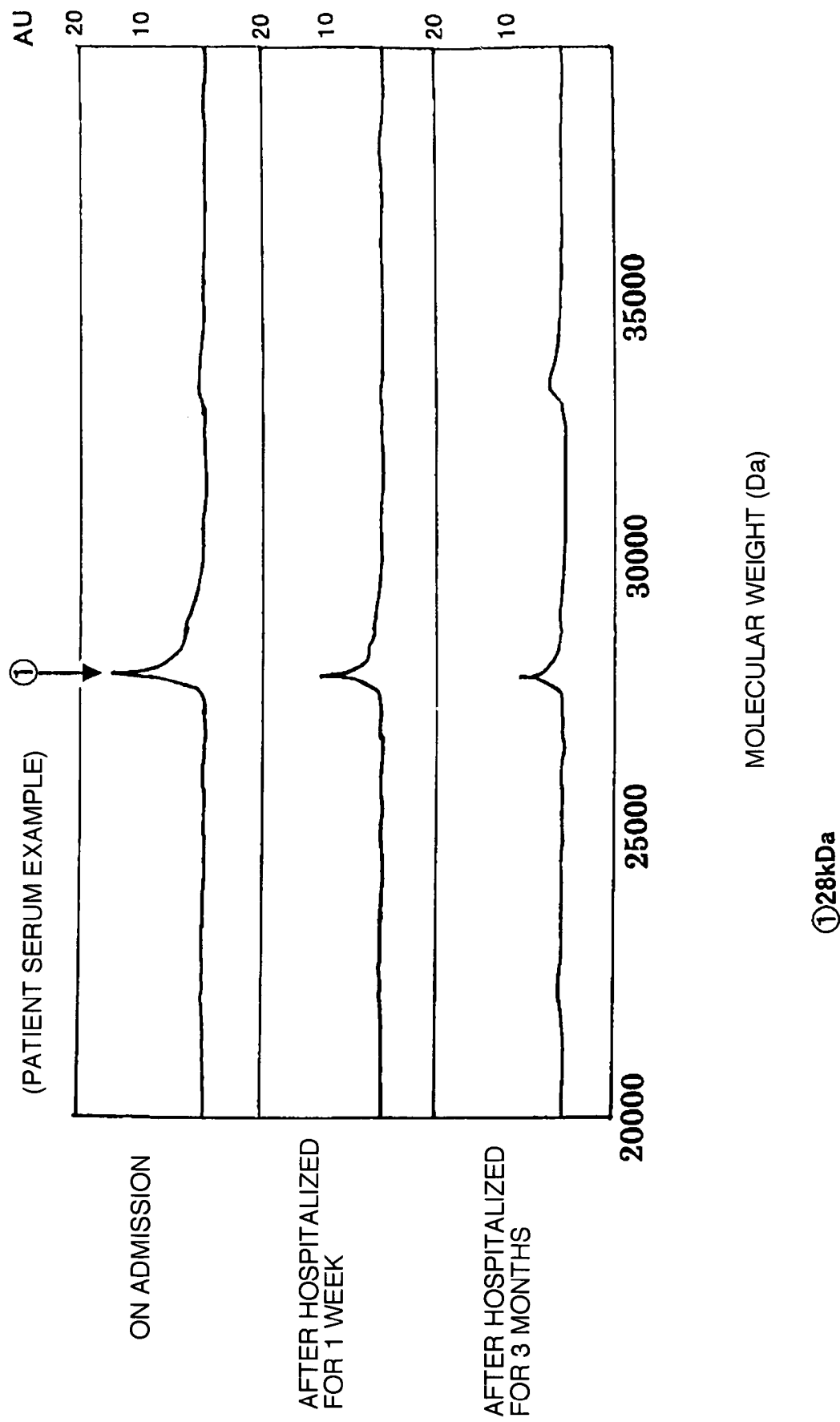
FIG. 1 shows the measurement results obtained from the serum of a patient with alcoholic liver trouble by the use of SAXII chips by utilizing Protein Chip System available from Ciphergen Biosystems Inc. From the decrease in height of the peak, it can be seen that the level of the 28 kDa protein (apolipoprotein AI) decreases in the serum gradually with the lapse of time in the order of the level at the time of admission, the level after hospitalization for 1 week and the level after hospitalization for 3 months.

The present invention is explained below in further detail.

The proteins that have been found to be utilizable as marker proteins for diagnosing liver disease by the present invention are a protein which is a human fibrinogen α-E chain decomposition product and has a molecular weight of 5,900 (hereinafter referred to as the 5.9 kDa protein), a protein which is an apolipoprotein AII decomposition product and has a molecular weight of 7,800 (hereinafter referred to as the 7.8 kDa protein), and a protein which is apolipoprotein AI and has a molecular weight of 28,000 (hereinafter referred to as the 28 kDa protein). The 5.9 kDa protein, the 7.8 kDa protein and the 28 kDa protein are proteins having the amino acid sequences shown as SEQ ID NOs: 1, 2 and 3, respectively, in the sequence listing.

The individual proteins are explained below. The 5.9 kDa protein is a human fibrinogen α-E chain decomposition product, comprises 54 amino acids and has a theoretical molecular weight of 5904.2. The 7.8 kDa protein is a human apolipoprotein AII decomposition product, comprises 68 amino acids and has a theoretical molecular weight of 7753.8. The 28 kDa protein is apolipoprotein AI, comprises 243 amino acids and has a theoretical molecular weight of 28078.8. As to the 5.9 kDa protein and the 7.8 kDa protein among the above proteins, the present invention has elucidated their presence in blood and their clinical significance in liver troubles and the like for the first time. The 5.9 kDa protein and the 7.8 kDa protein are novel proteins and novel marker substances. Apolipoprotein AI, the 28 kDa protein is a known protein, its clinical significance in lipid metabolism has been established, and its clinical measurement has heretofore been carried out.

The 5.9 kDa protein, 7.8 kDa protein and 28 kDa protein, which have been found to function as marker proteins for diagnosing liver disease by the present invention, are not limited to proteins having the amino acid sequences shown in the sequence listing but may be variants of these proteins which similarly function as marker proteins for diagnosing liver disease. That is, it should be sufficiently considered that the 5.9 kDa protein, 7.8 kDa protein and 28 kDa protein are very liable to be degraded by various endo- and exoproteases particularly in blood and tissues, resulting in changes of the total length of amino acids and the length of the sequence. In producing a recombinant protein, an amino acid variation capable of changing the antigenicity as slightly as possible should, of course, be given in order not to decrease the efficiency of expression. Therefore, there may also be used variants of the 5.9 kDa protein, 7.8 kDa protein and 28 kDa protein of the present invention which are proteins having 90% or more homology with the amino acid sequence of each of the proteins of the present invention (here, the term "homology" means the sameness of amino acids). The amino acid sequence of any of the variants may have a length changed by 15% or less, and the present invention also includes such a variant when it functions as a marker protein for diagnosing liver disease. The variants are preferably proteins having 95% or more homology, more preferably 98% or more homology. The homology of the amino acid sequence may be looked up in well-known software, for example, software obtained by adopting as a principle the reference method described in the method of Wilber, W. J., Lipman, D. J., et al. (Proc. Natl. Sci. USA, 80, 726-730, 1983). In addition, GENETYX (Software Development Co., Ltd.) or the like is commercial general-purpose software and is easily utilizable.

The variants of the 5.9 kDa protein, 7.8 kDa protein and 28 kDa protein, which are the marker proteins for diagnosing liver disease of the present invention, may also be variants which are proteins having an amino acid sequence formed by deletion, substitution or addition of one or more amino acid residues in each of the amino acid sequences shown as SEQ ID NOs: 1, 2 and 3 and have the same function as that of the above three proteins as marker proteins for diagnosing liver disease. As such variants, there are exemplified proteins obtained by the modification of less than 10%, preferably less than 5%, more preferably less than 2%, of the amino acid residues in the original amino acid sequence. The modification of the amino acid residues may be introduced as amino acid variation by a genetic technique generally known to those skilled in the art. The present invention also includes variants obtained by well-known modification such as post-translational modification, phosphorylation, acetylation, sugar chain addition, or the like.

Diagnosis of liver diseases becomes possible on the basis of the marker proteins for diagnosing liver disease found by the present invention and explained above. That is, the probability of the onset of a liver disease, the liver disease or the prognosis of the liver disease may be diagnosed by detecting or quantifying the above-mentioned marker proteins for diagnosing liver disease in a sample obtained from a patient who is suspected to have the liver disease.

As the sample usable in the present invention, there are exemplified serum, plasma, blood and urine collected from the patient who is suspected to have the liver disease.

All methods known at present may be adopted for detecting or quantifying the marker proteins for diagnosing liver disease of the present invention. The methods include, for example, mass spectrometry method, immunoassay method, electrophoresis method, liquid chromatography (LC) method and gas chromatography (GC) method.

As the mass spectrometry method, a method using a laser desorption/ionization-time of flight-mass spectrometer (LDI-TOF MS) is exemplified. As the laser desorption/ionization-time of flight-mass spectrometer, there may be exemplified surface enhanced laser desorption/ionization-time of flight-mass spectrometers (SELDI-TOF MS method) and matrix-assisted laser desorption/ionization-time of flight-mass spectrometers (MALDI-TOF MS method).

For example, when SELDI-TOF MS method is adopted, Protein•Biology•System II•Mass•Spectrometer (Ciphergen Biosystems, Inc.) developed by Ciphergen Biosystems, Inc. may be used. This machine is based on a protein chip technology comprising a combination of SELDI (surface enhanced laser desorption ionization) and a time-of-flight mass spectrometer. The details of the machine are disclosed in International Publication No. WO 01/25791 A2, JP-A-2001-28122 and the like. Usually, in SELDI-TOF MS method, a sample is pretreated, adsorbed on a chip and then loaded on a SELDI-TOF MS mass spectrometer. When the sample is serum, it is preferable to remove albumin from the system by using an adsorbent for albumin or washing the system with a buffer solution until the possession of electric charge by albumin owing to the ion exchange chip is ceased.

The protein chip used in such a method is not particularly limited so long as it can adsorb the marker proteins for diagnosing liver disease of the present invention. As the protein chip, there may be exemplified chips (referred to also as chemical chips) in which functional groups having hydrophobicity or affinity for proteins (e.g. ion exchange properties) have been modified, and chips (biochemical chips) having an antibody against the protein of interest immobilized thereon.

As another mass spectrometry method, a mass spectrometry method using ESI method (electrospray ionization) is exemplified. In the case of ESI method, it is often preferable to load a sample subjected to pretreatment such as protease treatment on a mass spectrometer connected directly to a separating means such as high performance liquid chromatography.

As the immunoassay method, there may be exemplified an immunoassay method in which a heretofore known protein is measured by preparing a polyclonal or monoclonal antibody against any of the marker proteins for diagnosing liver disease of the present invention. Such an immunoassay method includes enzyme immunoassay method (EIA method), immunoturbidimetry method (TIA method), latex immuno-agglutination method (LATEX method), electrochemiluminescence method, fluorescence method and the like. An immuno-chromatography method and a method using test paper are also effective. All of these methods are generally known to those skilled in the art and these generally known methods may be adopted as they are.

As the antibody usable in the above-mentioned immunoassay method, there are exemplified polyclonal or monoclonal antibodies prepared by generally used methods. These antibodies may be obtained by using a purified protein derived from human blood, specifically, the 28 kDa protein, the 7.8 kDa protein or the 5.9 kDa protein as an immunogen (an antigen). Although these proteins for preparing the antibodies may be obtained from human blood by purification, they may be obtained also by chemical synthesis by adopting a well-known peptide synthesis technique. Besides these antigens, proteins produced by cultured cells may also be used as an antigen. In addition, the employment of a full-length recombinant protein prepared by genetic engineering, its variant, or a portion of the recombinant protein or the variant is also a well-worn measure, and this measure may be utilized.

The monoclonal antibodies are produced by hybridomas obtained by immunizing an animal with an immunogen such as any of the above-exemplified various antigens, for example, the 28 kDa protein, the 7.8 kDa protein and the 5.9 kDa protein, namely, the marker proteins, and then fusing antibody-producing cells derived from the spleen or the like with myeloma cells.

The hybridomas may be obtained by the following method. That is, the antigen (e.g. the marker protein) obtained as described above is mixed with a well-known adjuvant such as Freund's complete or incomplete adjuvant, aluminum hydroxide adjuvant, pertussis adjuvant or the like to prepare an adjuvant liquid for sensitization, and this liquid is administered to an animal (e.g. a mouse or a rat) subcutaneously in the abdominal cavity or intravenously in the tail, in several portions at intervals of 1 to 3 weeks to immunize the animal. Although the amount of the antigen for the sensitization is usually chosen in the range of 1 µg to 100 mg, it is preferably about 50 µg in general. Although the number of immunizing operations is generally 2 to 7, various methods are known. Subsequently, antibody-producing cells derived from the spleen or the like are fused with myeloma cells or the like in a test tube. As to a method for the fusion, the fusion may be carried out by the use of a poly(ethylene glycol) (PEG) by the method of KÖhller and Milstein (Nature, 256, 495, 1975) which is already per se well known. The fusion may be carried out also by the use of Sendai virus or by an electrofusion method.

As to a method for selecting hybridoma capable of producing an antibody capable of recognizing the marker protein, from the fused cells, the selection may be carried out as follows. That is, the hybridoma is selected from colonies formed by cells surviving in HAT medium and HT medium in limiting dilution of the fused cells. When an antibody against the marker protein is contained in the supernatant of the culture medium for any of the colonies formed by the fused cells seeded into a 96-well plate or the like, a clone capable of producing a monoclonal antibody against the marker protein may be selected by an ELISA method in which the supernatant is placed on an assay plate having the marker protein immobilized thereon, and after the reaction, a secondary labeled antibody such as anti-mouse immunoglobulin-HRP labeled antibody is reacted with the above-mentioned antibody. As the labeling substance of the labeled antibody, there may be used enzymes (e.g. alkaline phosphatase), fluorescent substances, radioactive substances and the like besides HRP. Screening of specific antibodies against the marker proteins, respectively, may be conducted by carrying out, as a control, ELISA using an assay plate having only BSA bonded thereto as a blocking agent, simultaneously with the above-mentioned ELISA. That is, a clone is selected which is positive in any of plates having the marker proteins, respectively, immobilized thereon, and is negative in the ELISA method using BSA.

For example, hybridomas CN-1 and CN-2 established by the present inventor are clones capable of recognizing human 5.9 kDa protein specifically and are preferable examples. Hybridomas CN-1 and CN-2 were deposited as follows in Patented Organism Deposition Center (IPOD), Industrial Technology General Research Institute (Independent Administrative Corporation), Chuo-dairoku, Higashi 1-1-1, Tsukuba City, Ibaraki Prefecture, Japan 305-8566: hybridoma CN-1 was deposited as a receipt number IPOD FERM BP-08564 on Dec. 12, 2003 and hybridoma CN-2 was deposited as a receipt number IPOD FERM BP-08565 on Dec. 12, 2003.

The hybridoma is cultured on a medium usually used for cell culture, such as α-MEM, RPMI1640, ASF, S-clone or the like, and the monoclonal antibody may be recovered from the supernatant of the medium. The following is also possible: after a nude mouse, an animal from which the hybridoma is derived, is previously treated with pristane, cells are intraperitoneally injected into the animal to cause accumulation of ascites, and the monoclonal antibody is recovered from the ascites. As a method for recovering the monoclonal antibody from the supernatant or the ascites, a conventional method may be adopted. There are exemplified salting-out with ammonium sulfate, sodium sulfate or the like, chromatography, ion exchange chromatography, and affinity chromatography using protein A.

The 28 kDa protein, 7.8 kDa protein or 5.9 kDa protein in a sample may be accurately measured by the use of the monoclonal antibody according to the present invention purified by the above method. As a method for measuring the 28 kDa protein, 7.8 kDa protein or 5.9 kDa protein in a sample by an EIA method, there may be adopted a per se well known method using one or more monoclonal antibodies against the marker protein. An example of the method is described below. At first, the monoclonal antibody (antibodies) against the marker protein is directly or indirectly bonded to a per se well-known solid phase (e.g. a polystyrene, polypropylene, polycarbonate, polyethylene, nylon or polymethacrylate) by utilizing physical bonding, chemical bonding or affinity. The amount of the sensitizing antibody ranges usually from 1 ng to 100 mg/ml. A sample is added to the monoclonal antibody (antibodies) bonded to the solid phase by physical bonding, chemical bonding or affinity to carry out the reaction. After a definite period of the reaction, the solid phase is washed and a corresponding secondary labeled antibody (e.g. an anti-28 kDa protein secondary labeled antibody, an anti-7.8 kDa protein secondary labeled antibody or an anti-5.9 kDa protein secondary labeled antibody) is added to carry out the secondary reaction. The solid phase is washed again and DAB color-producing substrate or the like is added thereto to carry out the reaction. When HRP is used as the labeling substance, a known substrate such as DAB, TMB or the like may be used. The labeling substance is not limited to HRP. As the labeling substance, there are exemplified all recognizable substances including not only enzymes but also labeling metals (e.g. gold colloid and europium), various chemical or biological fluorescent substances (e.g. FITC, Rhodamine, Texas Red, Alexa and GFP) and radioactive substances (e.g. $^{32}$P and $^{51}$Cr).

The marker proteins may be measured also by a method other than the above-mentioned immunoassay method, such as an electrophoresis method, liquid chromatography (LC) method, gas chromatography (GC) method or the like. These methods are also generally known to those skilled in the art and these generally known methods may be adopted as they are.

By the method explained above, the probability of the onset of a liver disease, the liver disease or the prognosis of the liver disease may be diagnosed by detecting or quantifying the marker proteins for diagnosing liver disease in a sample obtained from a patient who is suspected to have the liver disease. When the diagnosis method of the present invention is practiced by the above-mentioned mass spectrometry, the diagnosis may be carried out also by analyzing the pattern of a spectrum obtained with a mass spectrometer. The diagnosis method of the present invention permits diagnosis of the probability of the onset of a liver disease in a habitual drinker or a problem drinker, diagnosis of a liver disease caused by drinking, such as hepatitis, liver cirrhosis or the like, and diagnosis of a usual liver disease. Furthermore, it also permits diagnosis of, for example, the progress of treatment of liver disease. The diagnosis method of the present invention is particularly suitable for diagnosis of alcoholic liver troubles, alcohol dependence and the like.

The present invention is illustrated in further detail with reference to the following examples, which should not be construed as limiting the scope of the invention.

EXAMPLE 1

Identification of a marker protein for diagnosing liver disease by the Use of SAXII protein chip arrays Using the sera of patients from whom informed consent had been obtained, a novel marker for liver trouble in the sera was searched for by the use of SAXII protein chip arrays (Ciphergen Biosystems, Inc.). The SAXII chip refers to a strong anion exchange chip and is characterized in that it binds thereto a negatively charged substance in a sample. The sera of the patients with alcoholic liver trouble immediately after admission, those 1 week after abstinence and those 3 months after abstinence and the sera of normal persons were used as samples.

(1) Method

A method for experimental operation of the protein chip array is briefly described below. Each serum sample was diluted 10-fold with a 8M urea (SIGMA)/1% CHAPS (SIGMA) solution. After on-ice treatment for 10 minutes, the serum sample was further diluted 10-fold with 50 mM Tris (SIGMA) buffer (pH 9.0) and centrifuged at 4,000 rpm for 5 minutes, and the supernatant was used as a diluted sample. An experiment was carried out by attaching the SAXII chip to a bioprocessor. The bioprocessor is a perforated plastic adaptor for simply forming three-dimensional wells on a metal chip. By such a method, a large volume of the diluted sample may be applied.

At first, 150 μL of 50 mM Tris buffer (pH 9.0) was added to the chip having wells formed thereon, and the chip was washed on a shaker for 5 minutes. After this procedure was carried out twice, 100 μL of the diluted sample previously obtained was added to the chip and shaken at room temperature for 20 minutes to be reacted with the chip. Then, the diluted sample was removed, and 150 μL of 50 mM Tris buffer (pH 9.0) was added to the chip, followed by washing on a shaker for 5 minutes. This procedure was repeated three times. Thereafter, the chip was washed twice with 400 μL of distilled water and then removed from the bioprocessor. After the chip dried, each spot having a protein adhered thereto was surrounded with PAPen (Zymed) and 0.5 μL of a saturated solution of sinapinic acid (Ciphergen Biosystems, Inc.) in 50% acetonitrile (Wako) and 0.5% TFA (Wako) was added twice to the spot. The protein chip arrays thus prepared were read with Protein•Biology•System II•Mass•Spectrometer (Ciphergen Biosystems, Inc.).

(2) Results

FIG. 1 shows typical measurement data obtained from the serum of a patient with alcoholic liver trouble at the time of admission. In this data format, the axis of abscissa may refer to the molecular weight of a protein in each sample detached from the SAXII protein chip, and the axis or ordinate may refer to a peak reflecting the amount of an analyte which has arrived at the detector at the aforesaid molecular weight. Therefore, it was found that as is clear from FIG. 1, a peak due to a protein having a molecular weight of 28 kDa was observed in the data for the patient with alcoholic liver trouble at the time of admission but was hardly observed after the admission. Accordingly, it was found that a liver disease may be diagnosed by using this 28 kDa protein as an indication.

EXAMPLE 2

Identification of marker proteins for diagnosing liver disease by the use of WCXII protein chip arrays Next, using exactly the same samples as in Example 1, novel markers for liver trouble in the sera were searched for by the use of WCXII protein chip arrays (Ciphergen Biosystems, Inc.). The WCXII chip refers to a weak cation exchange chip and is characterized in that it binds thereto a positively charged substance in a sample.

(1) Method

A method for experimental operation of the protein chip array is briefly described below and is substantially the same as in Example 1. Each serum sample was diluted 10-fold with a 8M urea (SIGMA)/1% CHAPS (SIGMA) solution. After on-ice treatment for 10 minutes, the serum sample was further diluted 10-fold with 50 mM sodium acetate (SIGMA) buffer (pH 6.5) and centrifuged at 4,000 rpm for 5 minutes, and the supernatant was used as a diluted sample. An experiment was carried out by attaching the WCXII chip to a bioprocessor. At first, 150 μL of 50 mM sodium phosphate buffer (pH 6.5) was added to the chip having wells formed thereon, and the chip was washed on a shaker for 5 minutes. After this procedure was carried out twice, 100 μL of the diluted sample previously obtained was added to the chip and shaken at room temperature for 20 minutes to be reacted with the chip. Then, the diluted sample was removed, and 150 μL of 50 mM sodium phosphate buffer (pH 6.5) was added to the chip, followed by washing on a shaker for 5 minutes. This procedure was repeated three times. Thereafter, the chip was washed twice with 400 μL of distilled water and then removed from the bioprocessor. After the chip dried, each spot having a protein adhered thereto was surrounded with PAPen (Zymed) and 0.5 μL of a saturated solution of sinapinic acid (Ciphergen Biosystems, Inc.) in 50% acetonitrile (Wako) and 0.5% TFA (Wako) was added twice to the spot. The protein chip arrays thus prepared were read with Protein•Biology•System II•Mass•Spectrometer (Ciphergen Biosystems, Inc.).

(2) Results

Figure 2:
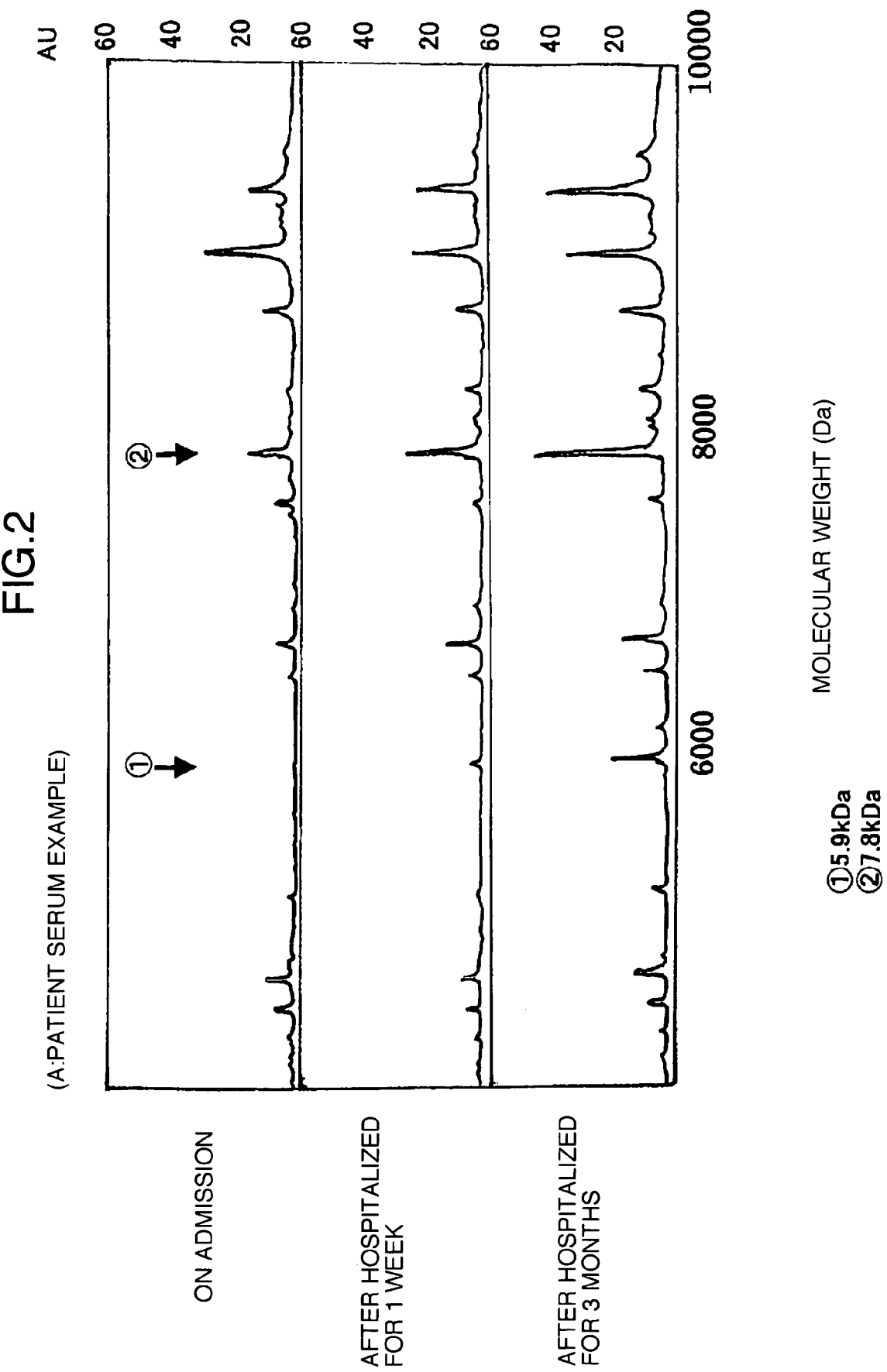
FIG. 2 shows the measurement results obtained from the serum of a patient with alcoholic liver trouble by the use of WCXII chips in the same manner as in FIG. 1. It can be seen that the blood levels of (1) the 5.9 kDa protein and (2) the 7.8 kDa protein increase with treatment with the lapse of time from the blood levels at the time of admission.
Figure 3:
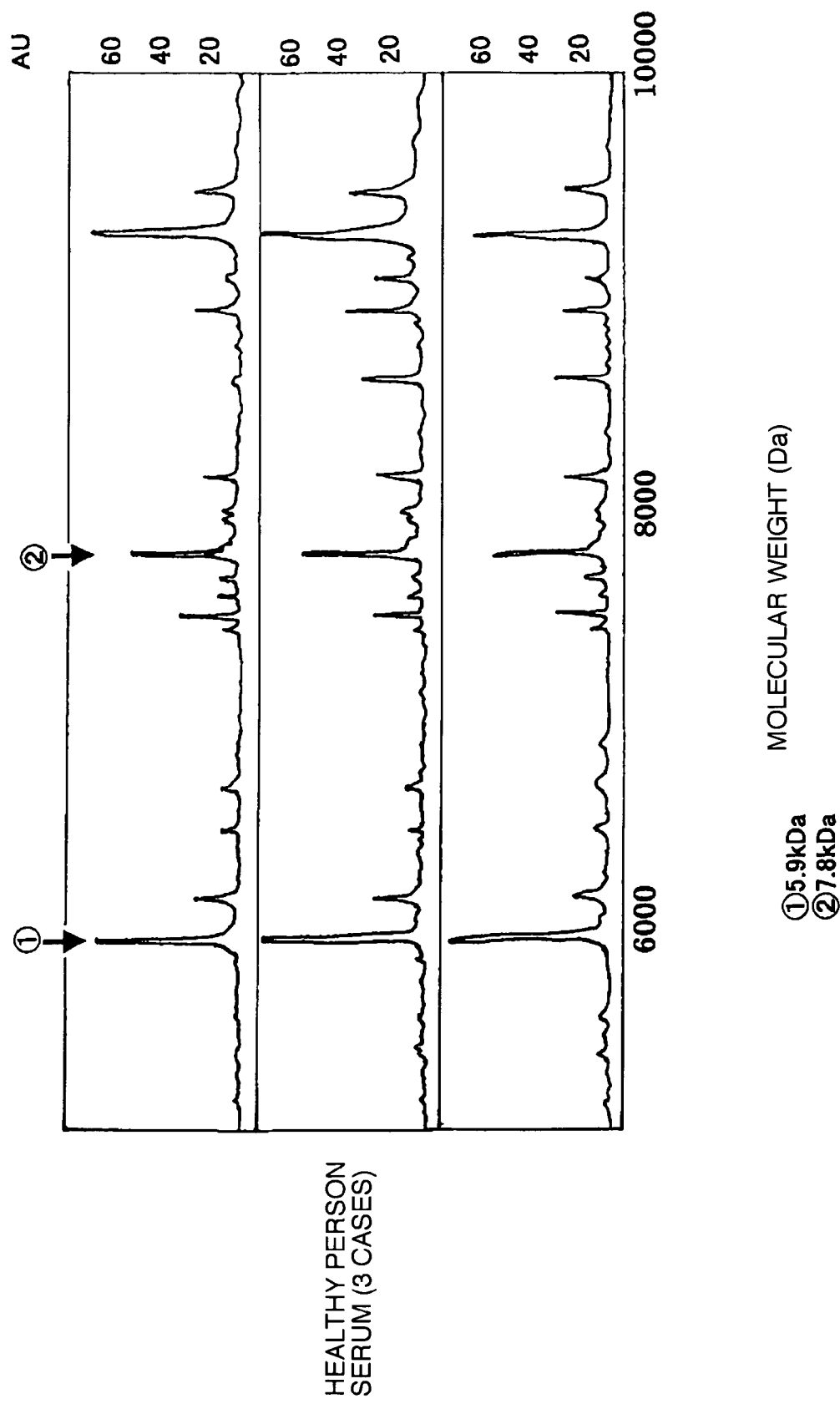
FIG. 3 shows the measurement results obtained from the serum of a healthy person by the use of WCXII chips in the same manner as in FIG. 1. The blood levels of (1) the 5.9 kDa protein and (2) the 7.8 kDa protein are definite high levels, and comparison between FIG. 2 and FIG. 3 indicates that these proteins are decreased by the disease.

FIG. 2 shows typical measurement data obtained from the serum of a patient with alcoholic liver trouble at the time of admission. FIG. 3 shows measurement data for normal persons. The following was found: as is clear from FIG. 3, the peaks at a molecular weight of 5,900 Da (the 5.9 kDa protein) and a molecular weight of 7,800 Da (the 7.8 kDa protein) are high in the data for the normal persons, but these peaks are hardly observed in the data shown in FIG. 2, i.e., the data for the patient with alcoholic liver trouble immediately after admission. The heights of the peaks due to the 5.9 kDa protein and the 7.8 kDa protein increase with treatment and clearly indicate the effect of the treatment. It was found that these proteins may be used as marker proteins for diagnosing liver disease.

EXAMPLE 3

Identification of the 28 kDa Protein (1) The 28 kDa protein found by the SAXII protein chip experiment was purified from a serum sample with FPLC Pharmacia LKB (Amersham Pharmacia Biotech AB) by the use of a HiTrap Q column under the following conditions: 50 mM Tris buffer (pH 9.0) and a flow rate of 2 ml/min. Thus, the 28 kDa protein of interest could be purified as a substantially single fraction. This fraction was confirmed as follows by electrophoresis. The fraction was mixed with 2× sample buffer (0.25 M Tris-HCl (pH 6.8), 4% SDS, 20% glycerol, 0.01% BPB and 10% β-mercaptoethanol) in the ratio of 1:1 and treated at 90° C. for 2 minutes. The fraction thus treated was used in the electrophoresis. The electrophoresis was carried out at 10 mA by the use of 15 to 25% polyacrylamide gradient gel (Perfect NT Gel System Products).

Figure 4:
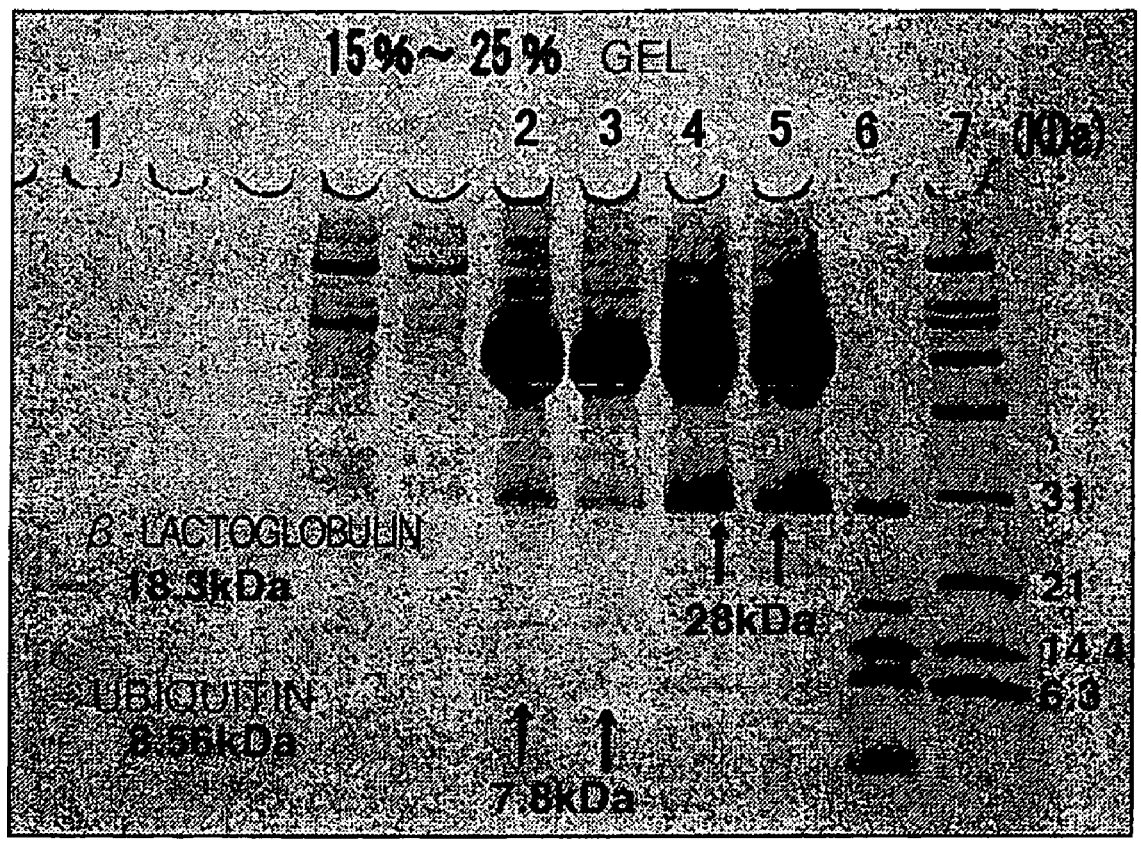
FIG. 4 shows the result of electrophoresis of the 7.8 kDa protein and the 28 kDa protein by SDS-PAGE. It can be seen that the samples contain the proteins of interest, respectively.

(2) As shown in each of the lanes 4 and 5 in FIG. 4, a band was confirmed at a position corresponding to 28 kDa, by Coomassie Brilliant Blue staining using Coomasie Tablet R-350 (Phast GI Blue R).

(3) Then, the band of the gel was excised and peptides were separated by an In-Gel digestion method. In brief, the piece of the gel obtained by excision was washed twice and then treated overnight with trypsin at 35° C. Thereafter, the sample treated with trypsin was purified by reversed phase HPLC. As to the purification conditions, gradient elution with 0.1% TFA and 0.09% TFA 90% acetonitrile was carried out by the use of a TSK gel ODS-80Ts QA (TOSOH) column.

The internal amino acid sequences of the resulting 28 kDa protein fragments were determined. The amino acid sequence of the 28 kDa protein is shown as SEQ ID NO: 3 in the sequence listing. As the result of amino acid sequencing of the 28 kDa protein fragments, the 28 kDa protein was found to be human apolipoprotein AI on the basis of the internal amino acid sequences of the 28 kDa protein fragments.

(4) Then, apolipoprotein AI levels were measured for the same serum samples as used in the chip experiments by an immunoassay method using the known autoanalyzer described in Example 6, to obtain the results shown in Table 1. From the immunoassay results, it was found that apolipoprotein AI levels were clearly reduced after treatment in the samples obtained from the patients who had gained effect from the treatment. On the other hand, the height of the peak due to the 28 kDa protein (apolipoprotein AI) observed as a result of the protein chip experiment was also reduced by the treatment, namely, it reflected the effect of the treatment. Thus, it was found that there is a very high correlation between the result obtained by the immunoassay method and the result of the protein chip experiment, indicating that the height of the peak is utilizable for analyzing morbidity.

EXAMPLE 4

Identification of the 7.8 kDa Protein (1) Like the 28 kDa protein, the 7.8 kDa protein found by the WCXII protein chip experiment was also purified from a serum sample with FPLC Pharmacia LKB (Amersham Pharmacia Biotech AB) by the use of a HiTrap CM Sepharose FF column under the following conditions: 50 mM ammonium acetate buffer and a flow rate of 2 ml/min. Thus, the 7.8 kDa protein of interest could be purified. A fraction in which the 7.8 kDa protein had been confirmed by the protein chip experiment was confirmed by electrophoresis as follows. The fraction was mixed with 2× sample buffer containing SDS, in the ratio of 1:1 and treated at 90° C. for 2 minutes. The fraction thus treated was used in the electrophoresis. The electrophoresis was carried out at 10 mA by the use of 15 to 25% polyacrylamide gradient gel.

(2) As shown in each of the lanes 2 and 3 in FIG. 4, a band was confirmed at a position corresponding to 7.8 kDa, by Coomassie Brilliant Blue staining. As in Example 3 for the above-mentioned 28 kDa protein, a fraction containing substantially only this protein of 7.8 kDa was concentrated and then subjected to SDS-PAGE, and the 7.8 kDa band of interest was excised from the gel and peptides were separated by an In-Gel digestion method. This method is the same as in Example 3. In brief, the piece of the gel obtained by excision was washed twice and then treated overnight with trypsin at 35° C. Thereafter, the sample treated with trypsin was purified by reversed phase HPLC. As to the purification conditions, gradient elution with 0.1% TFA and 0.09% TFA 90% acetonitrile was carried out by the use of a TSK gel ODS-80Ts QA (TOSOH) column.

(3) The resulting 7.8 kDa protein fragments were subjected to amino acid sequencing and found to be derived from human apolipoprotein AI, on the basis of the internal amino acid sequences of the 7.8 kDa protein fragments. However, the theoretical molecular weight of full-length human apolipoprotein AI is 11432.4. That is, the 7.8 kDa protein was found to be a human apolipoprotein AI decomposition product. The amino acid sequence of the 7.8 kDa protein is shown as SEQ ID NO: 2.

EXAMPLE 5

Identification of the 5.9 kDa Protein (1) The 5.9 kDa protein found by the WCXII protein chip experiment was purified from a serum sample with FPLC Pharmacia LKB (Amersham Pharmacia Biotech AB) by the use of a HiTrap CM Sepharose FF column under the following conditions: 50 mM ammonium acetate buffer and a flow rate of 2 ml/min. Thus, the 5.9 kDa protein of interest could be purified. A fraction having a high content of the 5.9 kDa protein was checked again by a protein chip method, concentrated and then further purified by HPLC (TOSOH). The purification conditions were as follows: a Sephasil protein C4 column (Amersham Pharmacia Biotech AB), an acetonitrile gradient, and 1 mL/min.

(2) The fraction was checked again by a protein chip method, concentrated by freeze-drying and then subjected to amino acid sequencing. As a result of the amino acid sequencing of the purified 5.9 kDa protein, this protein was found to be a human fibrinogen α-E chain decomposition product. That is, since the molecular weight of full-length human fibrinogen α-E chain is 72488.3, the 5.9 kDa protein was found to be a human fibrinogen α-E chain decomposition product. The amino acid sequence of the 5.9 kDa protein is shown as SEQ ID NO: 1.

Figure 5:
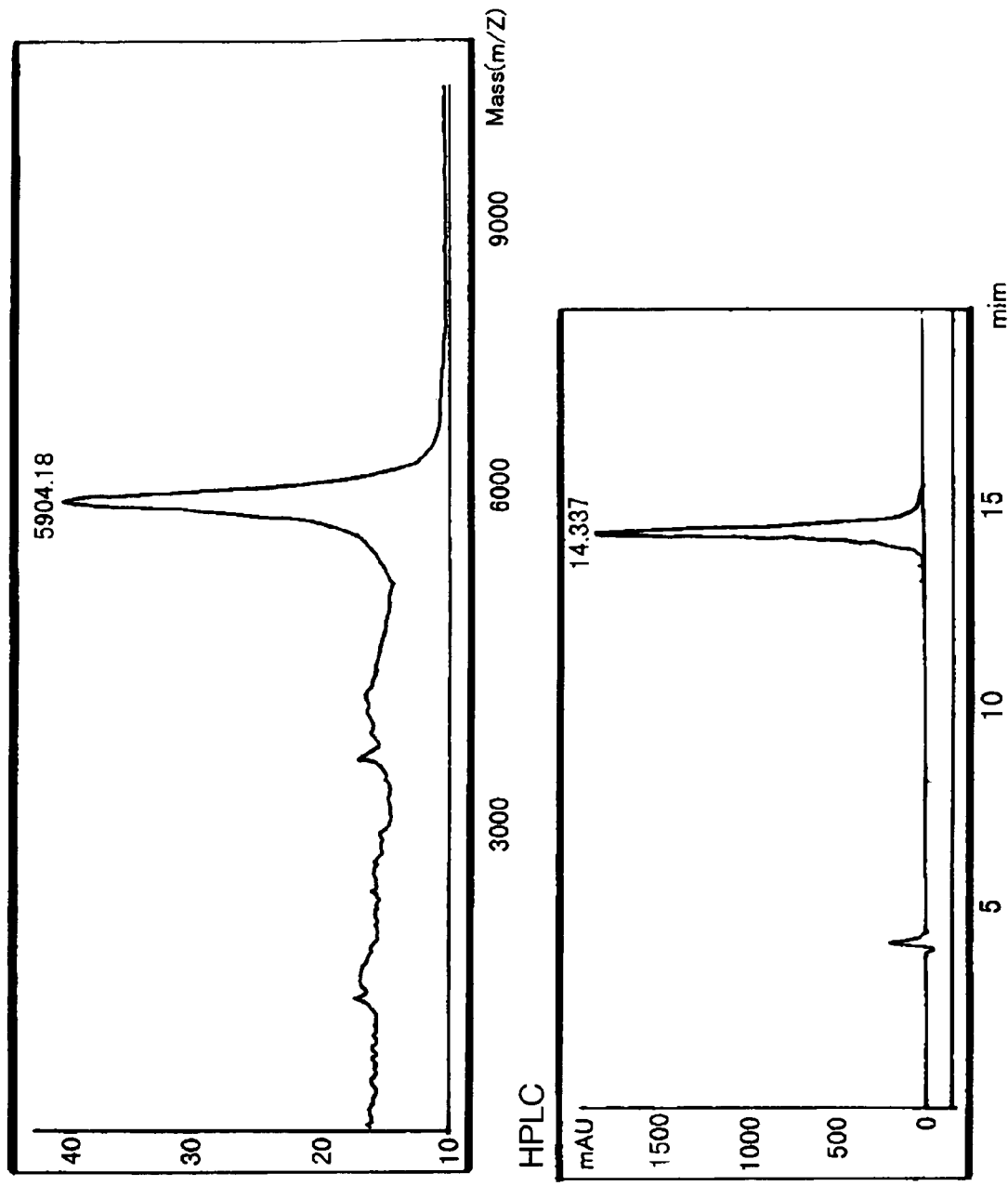
FIG. 5 shows the mass spectrometry value and HPLC data of synthetic 5.9 kDa protein. It can be seen that the mass spectrometry value agrees with the theoretical value.

In addition, in order to confirm the accuracy of the amino acid sequence of the 5.9 kDa protein, a protein having this amino acid sequence was wholly and chemically synthesized. The molecular weight of the chemically synthesized protein having 54 amino acids was 5904.1 which agreed with the theoretical value (FIG. 5). Furthermore, this synthetic protein was compared with an actual sample. An experiment was carried out by the use of exactly the same WCXII protein chip arrays (Ciphergen Biosystems, Inc.) as in Example 2. In the experiment, the synthetic protein was reacted in a concentration of 100 ng/mL as a sample and compared with the actual sample. The results are shown in FIG. 6. As a result, a peak due to the synthetic protein showed a behavior coinciding with a peak due to the 5.9 kDa protein in the serum sample. By these results, it was confirmed that the 5.9 kDa protein in the serum had the amino acid sequence shown as SEQ ID NO: 1.

EXAMPLE 6

Comparison Between Diagnosis in Patients with Alcoholic Liver Trouble Based on the Marker Proteins for Diagnosing Liver Disease of the Present Invention and that Based on Conventional Markers for Hepatitis (1) Method Measured values for conventional markers for hepatitis were obtained by using the same sera as used above, i.e., the sera of the 16 inpatients with alcoholic liver trouble immediately after admission, those after 1 week of hospitalization and those after 3 months of hospitalization. Measurement with an autoanalyzer was carried out as follows. AST, GGT, TG, Apo AI and Apo AII were measured with Hitachi 7150 analyzer (HITACHI). As reagents, N-assay L GOT (AST) (Nittobo), N-assay L γ-GTP-H (GGT) (Nittobo), N-assay TG L (TG) (Nittobo), N-assay TIA Apo AII-H (Apo AI) (Nittobo) and N-assay TIA Apo AII (Apo AII) (Nittobo) were individually used. FDP and FDP-E were measured with LPIA-S500 (Diayatron) by using predetermined parameters. In this measurement, LPIA FDP latex and LPIA FDP-E latex (Teikoku Hormone MFG. Co., Ltd.) were used as reagents. For comparison, the results of measurement using protein chips are expressed by numeral values on the basis of peaks. The units of the numeral values are arbitrary units.

(2) Results

Table 1 shows the following items in the common sera of patients hospitalized with alcoholic liver trouble: the levels of biochemical measurement markers for clinical examination (AST, GGT and TG), the levels of immunological measurement markers (Apo AI, Apo AII, FDP and FDP-E) and the results of measurement of the marker proteins for liver disease of the present invention by a protein chip method. In the first and second columns (the "FDP-E 5,900 Da" column and the "Apo AII 7,800 Da" column) from the right of Table 1, there are shown measured values obtained by measuring the 5.9 kDa protein and the 7.8 kDa protein, i.e., the marker proteins for diagnosing liver disease of the present invention, by a method using the same protein chips as in Example 2. In the sixth column (the "Apo AI" column) from the right of Table 1, there are shown measured values obtained by measuring the 28 kDa protein, i.e., the marker protein for diagnosing liver disease of the present invention, by a conventional method.

Table 2 shows measured values obtained by measuring the 5.9 kDa protein (FDP-E 5,900 Da) and the 7.8 kDa protein (Apo AII 7,800 Da), i.e., the marker proteins for diagnosing liver disease of the present invention, in serum samples from healthy persons.

Table 3 shows average measured values obtained by measuring the 5.9 kDa protein and the 7.8 kDa protein in the inpatients with alcoholic liver disease by a protein chip method.

TABLE 1

Changes of clinical examination values in patients with alcoholic liver trouble after abstinence

| | | AST U/L | GGT U/L | TG mg/dL | Apo AI mg/dL | Apo AII mg/dL | FDP μg/mL | FDP-E ng/mL | FDP-E 5,900Da AU | Apo AII 7,800Da AU |
|---|---|---|---|---|---|---|---|---|---|---|
| No. 1 | On admission | 34 | 542 | 672 | 144 | 37.3 | 2.99 | 110.32 | 11.7 | 9.9 |
| | After hospitalized for 1 week | 39 | 559 | 246 | 121 | 27.8 | 2.76 | 135.69 | 24.2 | 10.9 |
| | After hospitalized for 3 months | 25 | 121 | 142 | 79 | 17.4 | 1.63 | 80.20 | 20.8 | 6.1 |
| No. 2 | On admission | 13 | 9 | 103 | 88 | 15.0 | 3.57 | 77.28 | 0 | 3.1 |
| | After hospitalized for 1 week | 30 | 16 | 98 | 94 | 15.1 | 3.69 | 136.11 | 1.0 | 11.7 |
| | After hospitalized for 3 months | 15 | 3 | 173 | 95 | 20.8 | 2.65 | 126.56 | 1.8 | 20.0 |
| No. 3 | On admission | 42 | 68 | 100 | 155 | 38.2 | 1.37 | 70.18 | 0 | 0 |
| | After hospitalized for 1 week | 22 | 45 | 91 | 105 | 26.0 | 7.05 | 592.26 | 0 | 1.7 |
| | After hospitalized for 3 months | 18 | 19 | 117 | 104 | 21.5 | 15.96 | 1257.50 | 0.7 | 5.0 |
| No. 4 | On admission | 86 | 1452 | 150 | 234 | 45.0 | 3.39 | 93.30 | 0.5 | 7.9 |
| | After hospitalized for 1 week | 21 | 701 | 73 | 112 | 26.1 | 5.24 | 347.94 | 3.5 | 12.6 |
| | After hospitalized for 3 months | 15 | 24 | 68 | 95 | 17.7 | 7.27 | 516.60 | 17.7 | 21.1 |
| No. 5 | On admission | 24 | 74 | 93 | 95 | 21.8 | 0.31 | 35.11 | 0.8 | 2.4 |
| | After hospitalized for 1 week | 23 | 64 | 139 | 86 | 21.0 | 1.36 | 47.86 | 4.8 | 16.1 |
| | After hospitalized for 3 months | 35 | 160 | 154 | 80 | 18.5 | 3.27 | 71.87 | 6.2 | 18.1 |
| No. 6 | On admission | 44 | 108 | 141 | 149 | 37.7 | 1.56 | 42.53 | 9.2 | 12.1 |
| | After hospitalized for 1 week | 25 | 64 | 117 | 98 | 26.0 | 3.56 | 248.95 | 48.0 | 21.4 |
| | After hospitalized for 3 months | 17 | 24 | 109 | 83 | 19.3 | 8.88 | 743.54 | 58.0 | 20.0 |
| No. 7 | On admission | 37 | 111 | 119 | 218 | 46.5 | 2.54 | 90.77 | 0 | 0 |
| | After hospitalized for 1 week | 27 | 174 | 77 | 157 | 33.7 | 2.05 | 91.00 | 23.0 | 18.4 |
| | After hospitalized for 3 months | 19 | 26 | 81 | 95 | 23.3 | 1.58 | 50.95 | 21.7 | 10.4 |
| No. 8 | On admission | 40 | 61 | 170 | 183 | 33.3 | 3.87 | 127.00 | 1.7 | 3.3 |
| | After hospitalized for 1 week | 24 | 57 | 65 | 113 | 22.7 | 3.17 | 189.23 | 0 | 5.7 |
| | After hospitalized for 3 months | 22 | 36 | 113 | 101 | 20.6 | 2.35 | 105.10 | 1.8 | 6.9 |
| No. 9 | On admission | 20 | 77 | 244 | 114 | 28.4 | 4.33 | 118.19 | 0 | 0.4 |
| | After hospitalized for 1 week | 25 | 65 | 121 | 109 | 24.9 | 50.13 | 330.58 | 0 | 7.1 |
| | After hospitalized for 3 months | 24 | 36 | 260 | 109 | 24.0 | 5.33 | 270.77 | 1.7 | 14.0 |
| No. 10 | On admission | | | | | | | | 2.0 | 5.6 |
| | After hospitalized for 1 week | 55 | 232 | 67 | 69 | 18.5 | 13.52 | •915.69 | 8.7 | 16.1 |
| | After hospitalized for 3 months | 17 | 41 | 54 | 107 | 20.6 | 0.87 | 35.35 | 1.7 | 21.4 |
| No. 11 | On admission | 38 | 81 | 187 | 151 | 34.5 | 2.82 | 58.02 | 15.8 | 19.3 |
| | After hospitalized for 1 week | 20 | 67 | 98 | 116 | 28.1 | 6.33 | 554.17 | 56.0 | 26.4 |
| | After hospitalized for 3 months | 22 | 18 | 74 | 104 | 18.1 | 15.51 | 1310.60 | 52.0 | 18.6 |
| No. 12 | On admission | 18 | 37 | 103 | 135 | 24.8 | 1.91 | 43.10 | 0 | 11.7 |
| | After hospitalized for 1 week | 17 | 31 | 110 | 126 | 19.6 | 1.78 | 68.85 | 0.8 | 6.4 |
| | After hospitalized for 3 months | 21 | 32 | 118 | 136 | 22.6 | 1.03 | 33.59 | 1.2 | 15.0 |
| No. 13 | On admission | 18 | 31 | 84 | 198 | 30.6 | 1.99 | 38.14 | 12.2 | 9.4 |
| | After hospitalized for 1 week | 100 | 23 | 72 | 154 | 22.7 | 6.74 | 342.92 | 32.8 | 13.9 |
| | After hospitalized for 3 months | 17 | 18 | 80 | 180 | 22.6 | 14.37 | 1118.50 | 45.0 | 15.0 |
| No. 14 | On admission | 63 | 44 | 333 | 154 | 39.5 | 3.07 | 96.96 | 0 | 3.1 |
| | After hospitalized for 1 week | 43 | 39 | 72 | 111 | 27.0 | 2.50 | 146.95 | 0.3 | 11.0 |
| | After hospitalized for 3 months | 37 | 26 | 159 | 92 | 23.2 | 4.73 | 382.86 | 0.3 | 12.1 |

TABLE 1-continued

Changes of clinical examination values in patients with alcoholic liver trouble after abstinence

|  |  | AST U/L | GGT U/L | TG mg/dL | Apo AI mg/dL | Apo AII mg/dL | FDP μg/mL | FDP-E ng/mL | FDP-E 5,900Da AU | Apo AII 7,800Da AU |
|---|---|---|---|---|---|---|---|---|---|---|
| No. 15 | On admission | 49 | 86 | 91 | 146 | 28.9 | 1.35 | 58.93 | 13.0 | 7.0 |
|  | After hospitalized for 1 week | 19 | 79 | 82 | 83 | 23.0 | 2.29 | 59.44 | 28.5 | 17.7 |
|  | After hospitalized for 3 months | 22 | 60 | 112 | 86 | 22.5 | 2.99 | 177.59 | 51.0 | 18.0 |
| No. 16 | On admission | 29 | 84 | 90 | 162 | 31.3 | 3.24 | 88.54 | 2.5 | 1.3 |
|  | After hospitalized for 1 week | 12 | 70 | 118 | 102 | 26.6 | 1.86 | 84.94 | 1.7 | 10.3 |
|  | After hospitalized for 3 months | 16 | 15 | 96 | 72 | 17.0 | 5.84 | 213.87 | 2.0 | 13.3 |

TABLE 2

Levels of 5.9 kDa and 7.8 kDa proteins in healthy persons

| Number of healthy persons (n = 12) | FDP-E 5.9 kDa AU | Apo A II 7.8 kDa AU |
|---|---|---|
| No. 1 | 59.1 | 35.1 |
| No. 2 | 51.7 | 32.0 |
| No. 3 | 62.5 | 42.8 |
| No. 4 | 63.1 | 44.0 |
| No. 5 | 89.2 | 95.4 |
| No. 6 | 58.5 | 42.2 |
| No. 7 | 64.6 | 45.5 |
| No. 8 | 66.2 | 44.6 |
| No. 9 | 23.1 | 56.9 |
| No. 10 | 55.4 | 51.7 |
| No. 11 | 63.7 | 52.0 |
| No. 12 | 36.0 | 24.6 |

TABLE 3

Average levels of 5.9 kDa and 7.8 kDa proteins

|  | FDP-E 5.9 kDa AU | Apo A II 7.8 kDa AU |
|---|---|---|
| Healthy persons (n = 12) | 57.76 | 47.23 |
| Immediately after admission | 4.34 | 6.03 |
| After hospitalized for 1 week | 14.58 | 13.00 |
| After hospitalized for 3 months | 17.73 | 15.63 |

Number of patients (n = 16)

As shown in Tables 1 to 3, the decrease of generally used AST and GGT levels and the recovery of these levels to normal level ranges reflected the effect of treatment on liver. However, the blood levels of the 5.9 kDa protein and the 7.8 kDa protein increased and clearly indicated the effect of treatment even when the generally used GGT level was not usable as an indication of the effect of treatment as in the case of sample No. 5 from a patient who was considered as a nonresponder. The GGT level does not always correlate with the degree of seriousness of a liver trouble or the cumulative alcohol intake. In addition, the change of the GGT level after alcohol drinking varies depending on individuals and there are a considerable number of so-called nonresponders who show no increase in the GGT level even after drinking a large volume of alcohol. Therefore, the novel proteins were considered to be effective in judging the treatment of these GGT nonresponders.

EXAMPLE 7

Correlation Between Alcohol Intake and the Marker Proteins of the Present Invention By the working examples described above, the usefulness of the novel markers for diagnosing liver disease found by the present invention was confirmed with respect to their specificity. The following experiment was carried out for further elucidation of the correlation between alcohol intake and the markers.

Method

An experiment was carried out by collecting samples only from healthy persons and alcohol-drinking patients whose alcohol intake was certain. In the experiment, these subjects were divided into three experimental groups, i.e., a group of healthy persons as nondrinkers, a group of patients having an alcohol intake corresponding to 1 go of sake and a group of patients having an alcohol intake corresponding to 3 go of sake. For these groups, measurements using protein chip methods, respectively, were carried out and the groups were compared with respect to each of the novel markers. The measuring methods using protein chips were exactly the same as described in the case of SAXII protein chip arrays in Example 1 and WCXII protein chip arrays in Example 2.

Results

Figure 7:
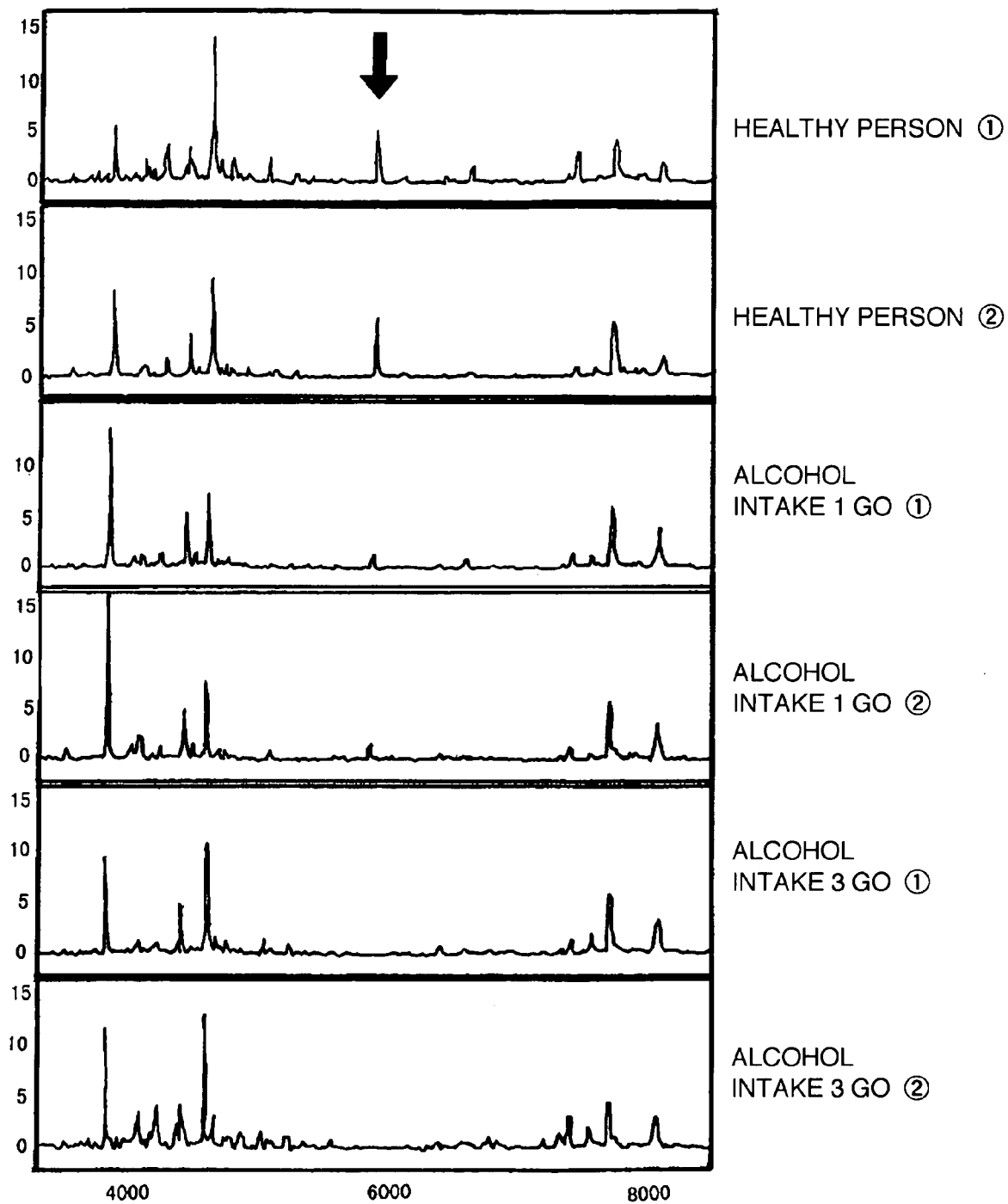
FIG. 7 shows the result of measuring the height of a peak at 5.9 kDa in the case of a serum sample from each of healthy persons and patients, who are various in alcohol intake, by the use of WCXII protein chip arrays by utilizing Protein Chip System available from Ciphergen Biosystems Inc. It was found that the height of the peak decreases depending on the alcohol intake.

The results are shown in FIG. 7. As a result, it was found that the heights of peaks due to all the novel marker proteins, respectively, for diagnosing liver disease vary depending on alcohol intake. Here, the results for, in particular, the 5.9 kDa protein are shown. The 5.9 kDa protein decreased depending on alcohol intake and it decreased to become substantially undetectable in the experimental group having an alcohol intake of 3 go. That is, it was found that the 5.9 kDa protein varies in amount, depending on alcohol intake and hence is a marker satisfactorily utilizable for estimation of alcohol intake. It was also found that the 5.9 kDa protein is utilizable as a marker for alcohol dependence.

EXAMPLE 8

Preparation of a Monoclonal Antibody

The following experiment was carried out for preparing an anti-5.9 kDa protein monoclonal antibody by using the completely synthetic 5.9 kDa protein obtained in Example 5, as an antigen.

(1) Immunization

The completely synthetic 5.9 kDa protein was diluted to a concentration of 1 mg/ml with phosphate buffer (pH 7.0), and 50 μg (50 μl) of the dilution was thoroughly mixed with 50 μl of Freund's complete adjuvant (WAKO) until emulsification was effected. The suspension thus prepared was intraperitoneally administered to a Balb/c female mouse aged 6 weeks (Nippon Clear Co., Ltd.) under anesthesia with diethyl ether. After 2 weeks, the same amount as above of the completely synthetic 5.9 kDa protein (50 μg/ml) was mixed with Freund's incomplete adjuvant (WAKO). By exactly the same procedure as in the case of the Freund's complete adjuvant, emulsification was effected to obtain a suspension and the mouse was sensitized with the suspension. Two weeks after the sensitization, the same procedure as above was carried out. For the fourth immunization, i.e., final immunization, a dilution of the completely synthetic 5.9 kDa protein (50 μg/ml) with phosphate buffer (pH 7.0) was prepared and then administered to the mouse by injection into the tail vein.

(2) Establishment of Hybridoma

Three days after the final immunization, the spleen was surgically removed from the mouse sensitized with the synthetic 5.9 kDa protein, under anesthesia with diethyl ether, and was aseptically dispersed to prepare splenocytes. Fusion was carried out according to the method of KÖhller and Milstein (Nature, 256, 495, 1975). The splenocytes were fused with myeloma cells P3-X63-Ag8-U1 (P3U1) by the use of a poly(ethylene glycol) (PEG4000) (MERK). As to the fusion ratio, the number of the splenocytes was $10 \times 10^7$, while the number of the myeloma cells P3-X63-Ag8-U1 (P3U1) was $2 \times 10^7$. That is, the fusion ratio of the splenocytes to the myeloma cells was 5:1. The fused cells were dispersed in 10% FCS (INVITROGEN) α-MEM (IRVINE) HAT (Cosmo Bio Co., Ltd.), seeded into a 96-wells microtiter culture plate (Sumitomo Bakelite Co., Ltd.) and then cultured under conditions of 37° C. and 5% $CO_2$.

(3) Screening

After about 2 weeks, the growth of colonies was confirmed and screening was conducted. A method for conducting the screening is described below. For producing a plate for the screening, the synthetic 5.9 kDa protein purified in the above working example was dissolved in phosphate buffer and fed into a 96-well plate (Nunc) in an amount of 1 μg/100 μl/well. The plate was allowed to stand at 4° C. for two nights and then washed three times with phosphate buffer containing 0.05% Tween 20. Each well was fed with 200 μl of 1.5% BSA solution in order to inhibit a nonspecific reaction, and the plate was allowed to stand overnight at 4° C. After the thus completed plate was washed three times with phosphate buffer containing 0.05% Tween 20, 100 μl of the culture supernatant was reacted in each well and the plate was further washed. Then, HRP-labeled anti-mouse immunoglobulin antibody (Zymed), a secondary antibody was added to carry out the reaction. After washing, 100 μl of a 3 mg/ml color-producing solution of o-phenylenediamine (OPD) (Nacalai tesque), a color-producing substrate for HRP, in citric acid was added to each well to cause coloration for a definite period. Then, 100 μl of 1N sulfuric acid was added to each well as a terminating solution and absorbance was measured at a measuring wavelength of 492 nm. Clones found to be positive by the above procedure were subjected to recloning by a limiting dilution method, and the resulting supernatants were checked again.

(4) Confirmation of Antibodies

Two clones, i.e., clones CN-1 and CN-2 were selected as clones which had recognized the synthetic 5.9 kDa protein, by confirming their reactivity with the synthetic 5.9 kDa protein by ELISA. Table 4 shows the results of assaying antibodies produced by these clones, by the use of a monoclonal antibody typing kit (Amersham Pharmacia Biotech).

TABLE 4

| Characteristics of monoclonal antibodies | | |
|---|---|---|
| Hybridoma | Class | Light chain |
| Clone CN-1 | IgM | κ |
| Clone CN-2 | IgM | κ |

(5) Preparation and Purification of the Monoclonal Antibodies

To a Balb/c female mouse aged 10 weeks (Nippon Clear Co., Ltd.) two weeks after administration of 0.5 ml of pristane (Aldrich) to the mouse were intraperitoneally administered $1 \times 10^7$ cells of each of the hybridomas CN-1 and CN-2 obtained. After about 2 weeks, ascites accumulated in the abdominal cavity of the mouse was surgically collected under anesthesia with diethyl ether. As a result of confirmation by the ELISA method adopted in the screening, by the use of the ascites stepwise diluted as a sample, it was found that the ascites contained a high concentration of the monoclonal antibody. The ascites was treated with 40% ammonium sulfate and dialyzed against PBS, and then the monoclonal antibodies CN-1 and CN-2 were purified by the use of S-300. As a result, a single band was confirmed at a molecular weight of about 900,000 when each of the monoclonal antibodies CN-1 and CN-2 had not been reduced, and two bands were confirmed at molecular weights of about 70,000 and 25,000 when each of them had been reduced with mercaptoethanol. The amount of each of the purified antibodies CN-1 and CN-2 was about 10 mg or more per mouse, namely, it was sufficient for industrial utilization.

EXAMPLE 9

Measurement of the 5.9 kDa Protein by EIA Method

There was investigated the possibility of measurement of the 5.9 kDa protein in a sample by ELISA method (EIA method) by the use of the two monoclonal antibodies CN-2 and CN-1 against the 5.9 kDa protein as a primary antibody and a secondary antibody, respectively.

(1) Method

For preparing a plate for ELISA, the primary antibody CN-2 was dissolved in phosphate buffer (pH 6.7) and fed into a 96-well plate (Nunc) in an amount of 1 μg/100 μl/well. The plate was allowed to stand at 4° C. for two nights and then washed three times with phosphate buffer containing 0.05% Tween 20. Each well was fed with 200 μl of 1.5% BSA solution in order to inhibit a nonspecific reaction, and the plate was allowed to stand overnight at 4° C. After the thus completed plate was washed three times with phosphate buffer containing 0.05% Tween 20, 100 μl of various concentrations of the synthetic 5.9 kDa protein was added to each well as a reference standard and the reaction was carried out at room temperature for 1 hour. After completion of the reaction, the plate was washed three times with phosphate buffer containing 0.05% Tween 20, and HRP-labeled CN-1 antibody as secondary antibody was added to carry out the reaction. After washing, 100 μl of a 3 mg/ml color-producing solution of o-phenylenediamine (OPD) (Nacalai tesque), a color-producing substrate for HRP, in citric acid was added to each well to cause coloration for a definite period. Then, 100

μl of 1N sulfuric acid was added to each well as a terminating solution and absorbance was measured at a measuring wavelength of 492 nm.

(2) Results

Figure 8:
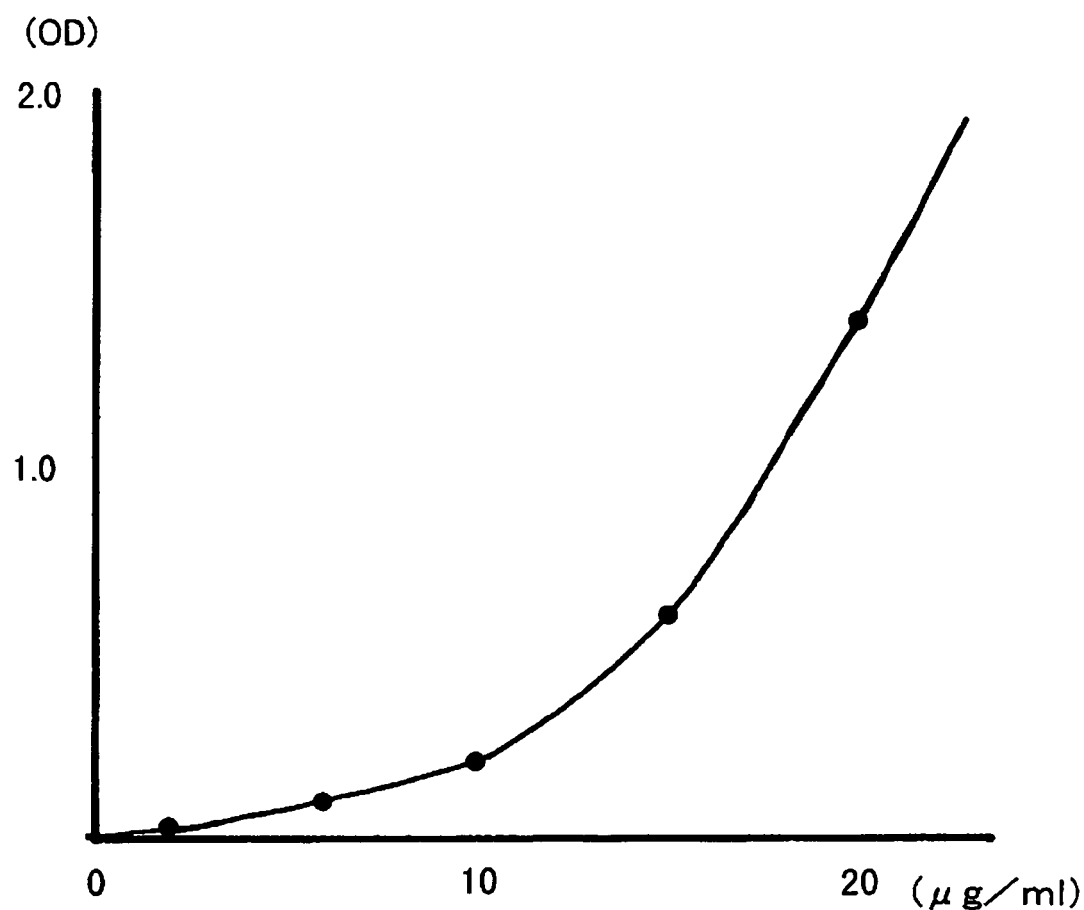
FIG. 8 shows the result of measuring absorbance by the use of an EIA method (a sandwich ELISA method) by using samples containing various concentrations of the 5.9 kDa protein. The axis of abscissa refers to the concentration of the 5.9 kDa protein and the axis of ordinate to absorbance measured. The absorbance increases depending on the concentration of the 5.9 kDa protein. That is, this result indicates that the concentration of the 5.9 kDa protein in the samples may be measured by the EIA method.

On the basis of coloration values measured for the various concentrations of the synthetic 5.9 kDa protein as described above, a standard curve for measuring the synthetic 5.9 kDa protein was prepared to obtain the result shown in FIG. 8. As can be seen from FIG. 8, absorbance increased depending on the concentration of the synthetic 5.9 kDa protein. That is, it was found that since the monoclonal antibodies CN-1 and CN-2 capable of recognizing the 5.9 kDa protein were different in epitope, the 5.9 kDa protein could be measured by using these antibodies in sandwich ELISA method.

INDUSTRIAL APPLICABILITY

As concretely described above, the marker proteins for diagnosing liver disease of the present invention may be used as an indication for accurately investigating the effect of judgment for the treatment of a patient with liver disease due to drinking to grasp the condition of the patient, even when the GGT level of the patient is high owing to a cause other than drinking as in the case of, for example, a nonresponder having a low reactivity with conventional markers for hepatitis (e.g. GGT), fatty liver accompanying corpulence, or a person who commonly uses a certain medicine. That is, GGT has a low specificity because it is increased by a cause other than drinking, such as a viral chronic liver trouble, corpulence, or continuous use of a certain medicine. On the other hand, the marker proteins for diagnosing liver disease of the present invention are advantageous in that their specificity is hopeful because their levels do not vary even in the case of viral liver cirrhosis. It is also found that these marker proteins are characterized by permitting easy handling of samples and giving a high reproducibility of measurement because substances to be measured in this case are peptides which are not dependent on biochemical enzymatic function. The diagnosis method of the present invention also permits diagnosis of the probability of the onset of a liver disease in a habitual drinker or a problem drinker and diagnosis of a liver disease caused by drinking, such as hepatitis, liver cirrhosis or the like. Moreover, it also permits diagnosis of, for example, the progress of treatment of such a liver disease. The diagnosis method of the present invention is suitable for diagnosis of, in particular, an alcoholic liver trouble, alcohol dependence or the like. In the diagnosis method of the present invention, diagnosis may be carried out by measuring the marker proteins by a generally used EIA method, immuno-chromatography, test paper or the like. The fact that the diagnosis can easily be carried out by such a generally used method is considered to be of great significance from the viewpoint of future preventive medicine in consideration of the present population of liver disease sufferers.

The invention claimed is:

1. An isolated protein consisting of the amino acid sequence shown as SEQ ID NO: 1 in the sequence listing.

* * * * *